United States Patent
Nyyssola et al.

(10) Patent No.: US 9,783,793 B2
(45) Date of Patent: Oct. 10, 2017

(54) POLYPEPTIDES AND ACTIVE FRAGMENTS OF POLYPEPTIDES HAVING AT LEAST ONE ESTERASE ACTIVITY

(75) Inventors: Antti Nyyssola, Espoo (FI); Hanna Kontkanen, Espoo (FI); Mari Hakkinen, Espoo (FI); Ville Pihlajaniemi, Espoo (FI); Markku Saloheimo, Espoo (FI); Johanna Buchert, Espoo (FI); Tiina Nakari-Setala, Espoo (FI)

(73) Assignee: Teknologian Tutkimuskeskus VTT (FI)

( * ) Notice: Subject to any disclaimer, the term of this patent is extended or adjusted under 35 U.S.C. 154(b) by 0 days.

(21) Appl. No.: 14/009,796

(22) PCT Filed: Apr. 11, 2012

(86) PCT No.: PCT/FI2012/050356
§ 371 (c)(1),
(2), (4) Date: Jan. 9, 2014

(87) PCT Pub. No.: WO2012/136898
PCT Pub. Date: Oct. 11, 2012

(65) Prior Publication Data
US 2014/0234921 A1   Aug. 21, 2014

(30) Foreign Application Priority Data
Apr. 6, 2011 (FI) ...................................... 20115328

(51) Int. Cl.
| | |
|---|---|
| C12N 9/18 | (2006.01) |
| C02F 3/34 | (2006.01) |
| D21B 1/02 | (2006.01) |
| C12P 7/40 | (2006.01) |
| C12P 7/62 | (2006.01) |
| C12N 9/20 | (2006.01) |
| C11D 3/386 | (2006.01) |
| D21C 5/00 | (2006.01) |
| D06L 1/12 | (2006.01) |
| D06M 16/00 | (2006.01) |
| D06L 4/40 | (2017.01) |

(52) U.S. Cl.
CPC .............. *C12N 9/18* (2013.01); *C02F 3/342* (2013.01); *C11D 3/38636* (2013.01); *C12N 9/20* (2013.01); *C12P 7/40* (2013.01); *C12P 7/62* (2013.01); *C12Y 301/01074* (2013.01); *D06L 1/12* (2013.01); *D06L 4/40* (2017.01); *D06M 16/003* (2013.01); *D21B 1/021* (2013.01); *D21C 5/005* (2013.01)

(58) Field of Classification Search
None
See application file for complete search history.

(56) References Cited

U.S. PATENT DOCUMENTS

| | | |
|---|---|---|
| 2002/0007518 A1 | 1/2002 | Kellis et al. |
| 2009/0162480 A1 | 6/2009 | Vikose-Nielsen et al. |
| 2009/0325240 A1 | 12/2009 | Daniell |

FOREIGN PATENT DOCUMENTS

| | | |
|---|---|---|
| CN | 101565902 | 10/2009 |
| DE | 19859971 | 6/2000 |
| WO | WO 9403578 | 2/1994 |
| WO | WO 2009/007510 | 1/2009 |
| WO | WO 2009042622 | 9/2009 |

OTHER PUBLICATIONS

Accession Q00298. Nov. 1, 1997.*
Chica et al. Curr Opin Biotechnol. Aug. 2005;16(4):378-84.*
Sen et al. Appl Biochem Biotechnol. Dec. 2007;143(3):212-23.*
Agrawal; The Performance of cutinase and pectinase in cotton scouring; PhD thesis; Sep. 30, 2005; University of Twente, The Netherlands.
De Barros, et al; Biosynthesis of ethyl caproate and other short ethyl esters catalyzed by cutinase in organic solvent; Oct. 2009; J Mol Cat B Enzym 60 (3-4); 178-185; Elsevier.
Carvalho, et al.; Cutinase structure, function and biocatalytic applications; Dec. 15, 1998; El J Biotech 1; 160-73; Elsevier Editorial System/Universidad Catolica de Valparaiso-Chile.
Davies, et al; Evidence for a role of cutinase in pathogenicity of *Pyrenopeziza brassicae* on brassicas; Aug. 2000; Physiol Mol Plant Pathol 57 (2); 63-75; Elsevier.
Fors, et al.; Cloning of the shark Po promoter using a genomic walking technique based on the polymerase chain reaction; May 1990; Nucleic Acids Research 18 (9); 2793-2799; Oxford Journals.
Gellissen (ed.); Production of recombinant proteins. Novel microbial and eukaryotic expression systems; May 19, 2005; Wiley-VCH Verlag Gmbh & Co.; Weinheim, Germany.
Halonen, et al,; A high thoughput profiling method for eutinolytic estrases; Jun. 8, 2009; Enz Microbial Technol 44 (6-7); 394-399; Elsevier.
Kontkanen, et al.; Characterisation of steryl esterase activities in commercial lipase preparations; Feb. 19, 2004; J Biotechnol 108 (1); 51-59; Elsevier.
Kontkanen, et al.; Novel *Coprinopsis cinerea* Polysterase That Hydrolyzes cutin and suerin; Jan. 2009; Appl Environ Microbiol 75 (7); 2148-2157; American Society for Microbiology.
Koller, et al.; Purification and characterization of cutinase from *Venturia inaequalis*; Mar. 1989; Phytopathology 79 (3); 278-283; American Phytopathological Society.
Pinto-Sousa, et al; Ester synthesis by a recombinant cutinase in reversed micelles of a natural phospholipid; Jan. 1994; Biocat 9 (1-4); 169-179; Taylor and Francis.

(Continued)

*Primary Examiner* — Christian Fonda

(57) ABSTRACT

The present invention relates to novel polypeptides, or fragments of polypeptides, genes encoding them and means for producing said polypeptides. In detail the invention relates to polypeptides having esterase, suberinase and/or cutinase activity at low pH. This invention relates also to compositions containing the polypeptides and methods of using the polypeptides.

14 Claims, 5 Drawing Sheets

(56) References Cited

OTHER PUBLICATIONS

Pio, et al.; Cutinases: properties and industrial applications; 2009; Adv Appl Microbiol 66 ; 77-95; Elsevier.
Platt, et al.; Improved DNA sequencing quality and efficiency using an optimized fast cycle sequencing quality and efficiency using an optimized fast cycle sequencing protocol; Jul. 2007; Bio Techniques 43 (1); 58-62; Informa Bio Sciences.
Salinas, et al.; Production of cutin hydrolyzing enzymes by Botrytis cinerea in vitro ; 1986; J Pathology 116; 299-307.
Sishiyama, et al; Studies on cutin-esterase II. Characteristics of cutin-esterase from *Botrytis cinerea* and its activity on tomato-cutin; 1970; Plant Cell Physiol 11; 937-945.
Thompson, et al.; Clustal W: improving the sensitivity of progressive multiple sequence alignment through sequence weighting, positron-specific gap penalties and weight matrix choice; Nov. 11, 1994; Nucleic Acids Res 22 (22); 4673-4680; Oxford Journals.
Trail, et al.; Diversity of cutinases from plant pathogenic fungi purification and characterization of two cutinases from *Alternaria brassicicola* ; Mar. 1993; Physiol Mol Plant Pathol 42; 205-220; Elsevier.
Van Der Vlugt-Bergmans, et al.; Cloning and expression of the cutinase A gene of *Botrytis cinerea*; Jan. 1997; Molecular Plant-Microbe Interactions 10 (1); 21-25; The American Phytopathological Society.
Database Uniprot, A7EQQ8_SCLS1; Scierotinia sclerotiorum (strain ATCC 18683/1980/Ss-1)(White mold) (*Whetzelinia sclerotiorum*), putative uncharacterized protein; & alignment with SQ ID No. 1; Sep. 11, 2007; retrieved from EBI Sep. 25, 2012; three pages.
Databse Uniprot, CUTI_BOTFU, Accession No. Q00298; Botryonia fuckeliana (Noble rot fungus) (Botrytis cinerea), cutimnase; & alignment with SEQ ID No. 1; Nov. 1, 1997; retrieved from EBI Sep. 21, 2012; three pages.
Databse Uniprot, CUTI_MONFR, Accession No. Q8TGB8; Monilinia fruticola cutinase; & alignment with SEQ ID No. 1; Jan. 11, 2003; retrieved from EBI Sep. 25, 2012; three pages.

* cited by examiner

```
Scsc        1  MKTSTQQLLSLLLLPLSTLAAPTGSIEAR----------------A TA
Bofu        1  MKTSAQQLLSALLLPLSVLAAPTGSIEAR----------------A SD
Mofr        1  MKTSAQQLLSLLLLPLSAIAAPTGEIEAR----------------A ST
ScCut       1  MKSTILFSALLSSGALAAPTVVEAVEARA----------------A SD
Fuso        1  M FFALTTLLAATASALPTSNPAQELEARQLGRTTRDDLINGNSAS RD
consensus   1  **                                            *  .

Scsc       35  TV ARG T IGT   VG PFLQA  SL SSAVSMTG--VD PA  PG
Bofu       35  TV ARG T TGT   VG PFLAA K AL SSSVTMNG--VD PA  PG
Mofr       35  TV ARG T TPT   IG QFLAA K SF G-SVTMNG--VP AAD PG
ScCut      35  TI ARG T PGT   AG PFFAA K QL GRATLTTQG-VD PAN AG
Fuso       51  IF ARG T TGN   G- SIASN  SAF KDGVWIQGVGGA RAT GD
consensus  51     .*** **   .**.  *   . *   *                * *  .

Scsc       83  --FLE GDSA SQT AKMVTSALSS  ETK   MS  C C  Q VHNAAKL
Bofu       83  --FLQ GDPA SQT ATMVTSTLSS  DTK   IS  C C  Q VHNAAKL
Mofr       82  --FLK GDPT SKV ANMVSSALSS  NTK   IS  C C  Q VHNAAKQ
ScCut      84  --FLA GDPA SQT ANDVKAALAA  DTK   MA  C C  Q VHNAAKL
Fuso      100  NALPR TSSA IRE LGLFQQANTK  DAT   AG  C C  A AAASIED
consensus 101       *     .    *               **   .. *****  *       *

Scsc      131  PAATMSK SSA   DPD GKA----QGLSSAK D  I HM  D  LGGD
Bofu      131  PAETTAK SSA   DPD GDP---QGVSADR D  I HA  N  QGGS
Mofr      130  PAATTAK AAA   DPD GSP---QGVPAAK K  I HA  N  QRGS
ScCut     132  G-GTMSQ NSA   DPD GQP---AGLSAAQ K  I HA  N  QGGA
Fuso      150  DSAIRDK AGT   YTK LQNRGR PNYPADR K  F NT  L  TGSL
consensus 151         .  *  **   *         .    *  .  *  **  .*     .

Scsc      178   LYA  T CM VTAA AFVKKAAGL-------
Bofu      178   LLA  T CM TTAA AFVKKAAGL-------
Mofr      177   LMP  T CM ATAA AFVKQVAGS-------
ScCut     178   LAP  T CQ AGTA SFVIAAAGL-------
Fuso      200   AAP  A CP ARGP PEFLIEKVRAVRGSA
consensus 201  .      ** ** *       *
```

Figure 1.

POLYPEPTIDES AND ACTIVE FRAGMENTS OF POLYPEPTIDES HAVING AT LEAST ONE ESTERASE ACTIVITY

FIELD OF THE INVENTION

This invention relates to novel polypeptides, particularly to polypeptides having cutinase activity also in acidic pH. The invention also relates to recombinant polynucleotides, vectors and host cells that are usable in producing said polypeptide, to method of obtaining said polypeptide and compositions comprising the polypeptide. Further, the invention relates to methods of hydrolysis of ester bonding and uses of the polypeptide.

DESCRIPTION OF RELATED ART

Cutin is an abundant biopolymer present in the protective, waxy layer on the surfaces of aerial parts of plants. It is composed of variably substituted fatty acids interlinked with ester bonds. The typical structural components of cutin are hydroxyl and epoxy substituted ω-hydroxy fatty acids with C16 and C18 carbon chains. The cutin polymer is formed via esterification of primary alcohols. Suberin is another common protective biopolymer. It is found for example in tree bark, cork and in roots. Suberin is composed of a polyphenolic domain and a polyester domain. The polyester domain is chemically similar to cutin, but may differ somewhat in its fatty acid composition (fatty acids with longer carbon chains may be present) and in the form of cross-linking Glycerol is a major suberin component in some species and acts as the cross-linker between the suberin monomers.

Cutinases are enzymes, which catalyze the hydrolysis of the ester bonds of cutin, suberin, lipids, waxes and other esters. All of the biochemically well-characterized cutinases are serine esterases, containing the Ser-His-Asp triad similar to serine proteases and several lipases (Carvalho et al., 1998). All known cutinases have a neutral or alkaline pH-optimum, with low or negligible activity at low pH. The cutinases that have been reported to be functional at slightly acidic pH include the following. In a report by Shishiyama et al. (1970) a cutinase from *Botrytis cinerea* was shown to have optimum activity at pH 5 with no detectable activity at pH 4.0 and below. Salinas et al. (1986) describe a *Botrytis cinerea* cutinase with a pH optimum between 5.5 and 6.0. However, no data is given on the activity of the enzyme at lower pH. In another report on a *Botrytis cinerea* cutinase a pH optimum of 5.6 was determined, but no information on the activity at other pH-values was given (van der Vlugt-Bergmans et al., 1997). A *Trichoderma reesei* cutinase has been reported to have a local pH optimum at pH 4 for p-nitrophenylbutyrate (pNPB) esterase activity. The effect of pH on the hydrolytic activity towards the natural substrates, cutin or suberin, were however not reported for this enzyme (WO2009007510). Trail and Köller (1993) describe two cutinases from the fungus *Alternaria brassicicola*, which have pH optima at 6.5 and at 8.5. These enzymes show only modest activity at pH 5.0. Köller and Parker (1989) describe a cutinase from *Venturia inaequalis* showing a pH optimum between pH 6.0 and 7.0. However, no data is given by the authors on the activity of this enzyme at pHs below pH 5.0.

Cutinases have been suggested for a number of uses of which only few are mentioned here. Cutinases could be used in detergents for dishwashing and laundry applications. Cutinases having an alkaline pH-optimum are suitable for use in alkaline detergents. Cutinases having an acidic to neutral pH-optimum could be suitable for rinse conditioners, for light duty products and for industrial cleaning products (WO9403578).

For use in the textile industry, a bioscouring method utilizing cutinases for the removal of the waxy layer present in cotton has been developed (Agrawal, 2005). Cutinases have also been used for modification of the surfaces of polyester fibers (US2002007518) and in antifelting of woolfabrics (CN101565902).

In addition to hydrolytic reactions cutinases can be utilized for catalyzing inter- and transesterification reactions as well as synthesis of esters (Pio and Macedo, 2009; Pinto-Sousa et al., 1994; de Barros et al., 2009). The use of cutinases for the detoxification of feed products contaminated by the heat-stable mycotoxin zearalenone has recently been patented (US2009162480). Cutinases have also been suggested for use in combination with other hydrolytic enzymes for the degradation of plant materials (US20090325240) and for pre-treating wood-containing material (WO2009042622).

Large amounts of cutin and suberin are present in low value waste materials produced by food, agriculture and forest industries. These waxy materials are hydrophobic and their structure is recalcitrant. They may thus impair the industrial processing of plant materials.

The use of polyesterases could improve the processing and exploitation of several plant materials, such as cereals, fruits, vegetables and berries, and also improve the release and recovery of valuable bioactive and functional components from these materials.

Cutin is for example present in the processing waste of fruits, vegetables and berries. Furthermore, the forest industry produces massive amounts of bark waste, of which suberin is a major component. These polyester materials provide a rich source of high value chemicals, which have potential use as raw materials for example in the production of lubricants and binders.

Many of these polyester containing materials described above are acidic. Despite their wide potential, applicability of the known cutinases is limited, since their reported cutinolytic and suberinolytic activities are either poor or nonexistent at low pH. That is, acidic materials cannot be hydrolyzed with the known cutinases. Furthermore, the pH range at which known cutinases are active is typically narrow. The known cutinases can thus be used only under restricted conditions, which is a remarkable disadvantage in industrial processes, especially when use of a mixture of enzymes is required. There is a need for cutinases that are stabile and active over a broad pH range from acidic to neutral. The present invention meets this need.

OBJECTS AND SUMMARY OF THE INVENTION

The aim of the present invention is to provide novel polypeptides or fragments of polypeptides. Particularly the aim of this invention is to provide polypeptides having esterase, and preferably cutinase, suberinase and/or lipase activity at acidic pH and polypeptides that are usable over a wide range of pHs. Further, the aim is to provide nucleotides encoding said polypeptides, means for production of said polypeptides and preparations containing polypeptides.

First aspect of the invention is a novel polypeptide. Characteristic to the polypeptide is that it comprises an amino acid sequence having at least 70% sequence identity to SEQ ID NO: 1 or fragment of said polypeptide.

The second aspect of the invention is a recombinant polynucleotide. Characteristic to the polynucleotide is that it comprises a nucleotide sequence having at least 80% identity to nucleotides from 52 to 606 of SEQ ID NO: 2 or to nucleotides from 7 to 561 of SEQ ID NO: 3, or a complementary strand thereof, or a codon optimized sequence of SEQ ID NO: 2.

The third aspect of the invention is a vector. Characteristic to the vector is that it comprises the polynucleotide of the invention.

The fourth aspect of the invention is a host cell. Characteristic to the host cell is that it has been transformed with the vector of the invention.

The fifth aspect of the invention is a method for obtaining the polypeptide of the invention. According to the invention the method comprises transforming a microorganism with a vector of this invention, culturing the transformed microorganism under conditions allowing the expression of said polynucleotide, and recovering the expressed polypeptide.

The sixth aspect of the invention is an enzyme preparation. Characteristic to the enzyme preparation is that it comprises the polypeptide or a fragment thereof according to the invention.

The seventh aspect of the invention is a method of hydrolysis of ester bonds. According to the invention the method comprises contacting material containing ester bonds with the said polypeptide or a fragment thereof according to this invention under conditions suitable for hydrolysis.

The eight aspect of this invention is a method of trans- or interesterification. According to the invention the method comprises contacting material to be esterified with the polypeptide or the fragment of this invention under conditions suitable for esterification.

Still the ninth aspect of this invention is a use of the polypeptide or a fragment of this invention, or enzyme preparation of this invention in food industry, pulp and paper industry, detoxification applications, textile industry, or in laundry and dishwashing applications, or in chemical syntheses.

Preferred embodiments and advantages of the invention are described in the following detailed description with reference to the attached drawings.

BRIEF DESCRIPTION OF THE DRAWINGS

FIG. 1. Alignment of the *Sirococcus conigenus* cutinase amino acid sequence with other fungal cutinase sequences. Abbreviations: Scsc—*Sclerotinia sclerotiorum* (GenBank XP_001558272), Boci—*Botrytis cinerea* (GenBank XP_001558272), Mofr—*Monilinia fructicola* (Uniprot Q8TGB8), ScCut—*Sirococcus conigenus*, Fuso—*Fusarium solani* f. sp. *pisi* (GenBank P00590). Identical residues are framed in black while similar residues are framed in grey. The three amino-acids (Ser, His, Asp) belonging to the catalytic triad are marked with rectangles.

DETAILED DESCRIPTION OF THE INVENTION

Figure 2:
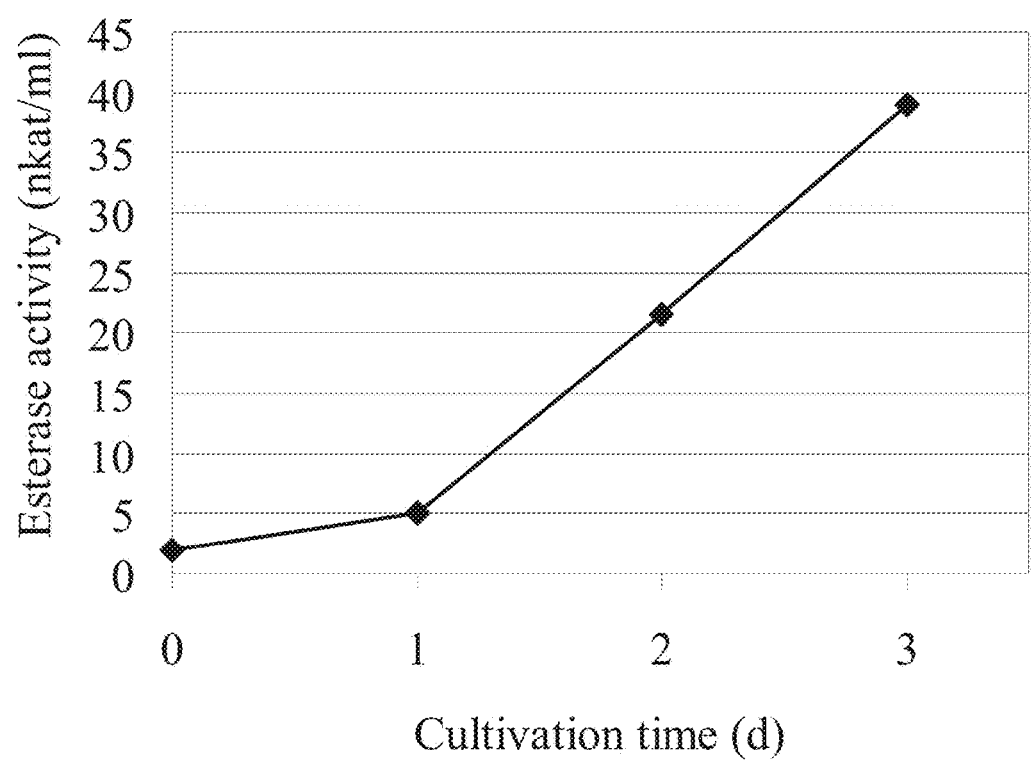
FIG. 2. pNPB-esterase activity (at pH 3.5) of the growth medium of the *Pichia pastoris* transformant expressing the gene for ScCut.

The invention provides novel polypeptides having a SEQ ID NO: 1 or a sequence showing at least 70% identity to SEQ ID NO:1.

In one embodiment of the invention the polypeptide comprises an amino acid sequence that has at least 70%, preferably at least 75%, 80%, 85%, 90%, 95%, 97% or 99% sequence identity to SEQ ID NO: 1 or fragment of said polypeptide. In further embodiment the polypeptide consists of an amino acid sequence that has at least 70%, preferably at least 75%, 80%, 85%, 90%, 95%, 97% or 99% sequence identity to SEQ ID NO: 1 or fragment thereof.

As used herein the term "identity" means the sequence identity between two amino acid or nucleotide sequences compared to each other. Particularly the identity means a global identity of respective fragments of the sequences. It is evident to a skilled man that e.g. a mature polypeptide is not comparable to a polypeptide with a signal peptide. The identity of the sequences is determined using ClustalW alignment (e.g. in using default settings and Blosum62 as the substitution matrix (Thompson et al., 1994).

In this connection term "fragment" means a part of SEQ ID NO: 1 being able to express at least one of the activities of the mature polypeptide. Preferably the activity of the fragment is at least 30% of the activity of the mature protein. In one embodiment the active fragment has at least part of any of the activities of the polypeptide as defined in SEQ ID NO: 1, preferably it has activity of at least 40%, more preferably 50%, 60% 70% 80%, 90% or even essentially the same activity as the mature protein (i.e. amino acids 18-202 of SEQ ID NO: 1, encoded by nucleotides 52-606 of SEQ ID NO: 2 and encoded by nucleotides 7-561 of SEQ ID NO: 3). In one embodiment the active fragment comprises at least 73 amino acids, preferably amino acids 116-188 of SEQ ID NO: 1. In this embodiment the identity to the fragment is at least 76%, preferably at least 80%, more preferably at least 85%, 90%, 95% or even 98%.

Particularly the polypeptides of this invention are esterase enzymes, which belong to the subclass EC 3.1.1 (Nomenclature of the International Union of Biochemistry and Molecular Biology) and which hydrolyze carboxylic acid esters with the formation of an alcohol and a carboxylic acid anion. Typically the enzymes of this invention have activity towards several substrates.

Polyesters are polymers which contain an ester functional group. Polyesters may be synthetic (such as for example polyethylene terephthalate, polycaprolactone and polylactic acid) or of natural origin (such as for example suberin and cutin).

Cutinases (cutin hydrolases, EC 3.1.1.74) are serine esterases containing typically the Ser, H is, Asp triad of serine hydrolases and catalyzing the hydrolysis of carboxylic ester bonds of cutin and suberin, but also of lipids, waxes and other polyesters and esters. Suberinase is an enzyme catalyzing the degradation of suberin. Lipases (triacylglycerol lipases EC 3.1.1.3) are esterases that hydrolyse water-insoluble substrates such as long-chain triglycerides at the interface between the substrate and water. Esterases such as carboxylesterases (EC 3.1.1.1) can also hydrolyze water-soluble esters of carboxylic acids.

In one embodiment of the invention the polypeptide or a fragment thereof has at least one esterase activity. In another embodiment the activity is a cutinase activity, in still another embodiment the activity is a suberinase activity and in still further embodiment the activity is a lipase activity. In more preferred embodiment the polypeptide or the fragment has two of the above defined activities, most preferably all three of said activities.

In one embodiment of the invention the polypeptide of the invention or a fragment thereof is active below pH 5; preferably below 4.5, more preferably below 4, below 3.5 or below 3.0, most preferably below 2.5 or even at about 2. Acidic conditions for cutinase treatment are preferable for example in processing food and feed products, since the risk of microbial contamination is reduced at low pH.

In one embodiment of the invention the polypeptide of the invention or a fragment thereof is active towards polyesters within pH 2.5-7.5; preferably within pH 3.5-6.5. A pH-optimum for cutin hydrolysis is in the range from pH 3.5 to 4.5. The polypeptide also has a local pH-optimum in the range from pH 6 to 7. Between these two optima the activity is also very high, more than 85% of the maximal activity. The pH optimum for pNPB-esterase activity is between 4.5 and 5.

In one embodiment the polypeptide or fragment thereof is active on fatty acid polyesters.

Figure 3:
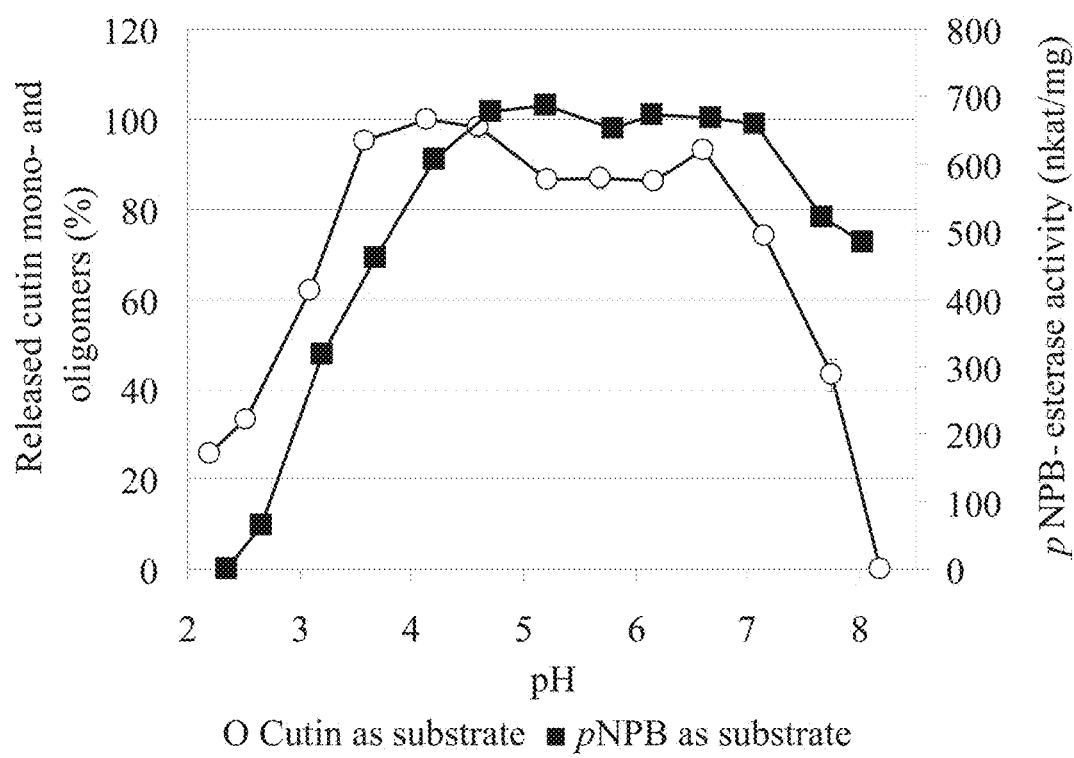
FIG. 3. The esterase (as hydrolysis of pNPB) and cutin hydrolyzing efficiency of ScCut. The esterase activities were determined kinetically at 25° C. The amounts of released cutin mono- and oligomers were determined at 40° C. for 24 h and are represented as percents of the maximum. The error bars represent standard deviations.
Figure 4:
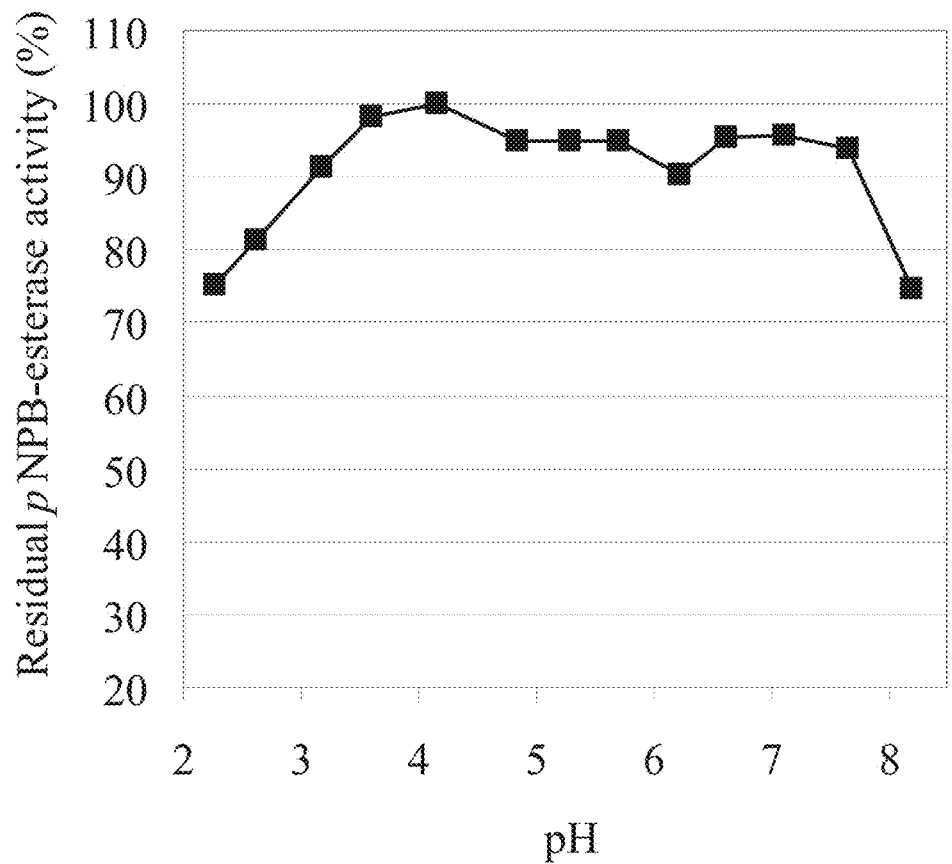
FIG. 4. Residual pNPB-esterase activity of ScCut after 24 h of incubation at 40° C.

Wide pH range for high activity (see Example 6 and FIGS. 3 and 4) makes the enzyme suitable for use under various process conditions, possibly in combination with other enzymes.

In one embodiment of the invention the polypeptide of the invention or a fragment thereof is stabile within the pH range of 2.0 to 8.0 at 40° C. or at lower temperature. In preferred embodiment the enzyme has 80%, more preferably 90% stability within the pH range of 3.5 to 7.5 at 40° C. or at lower temperature. Wide pH stability is an advantage in processes where the pH conditions are changing during the process. pH properties of the polypeptide of the invention are analyzed in Example 6.

The polypeptide (or its fragment) of the invention is active at low pH towards substrates of variable molecular masses ranging from polyesters such as cutin or suberin to smaller molecules such as pNPB. This can be a benefit when materials containing different types of esterified substances are hydrolyzed.

In one embodiment of the invention the polypeptide or a fragment thereof is obtained directly or indirectly from *Sirococcus*, preferably from *Sirococcus conigenus*. *Discella, Hypoderma, Hysterium* and *Phoma* are synonyms to *Sirococcus*. *Discella strobilina, Hypoderma conigenum, Hysterium conigenum, Phoma conigena*, and *Sirococcus strobilinus* are synonyms to *Sirococcus conigenus*. In this connection "obtained directly" means that the polypeptide or a fragment is produced by *Sirococcus*, whereas "obtained indirectly" means that the gene or the sequence information has essentially been derived from *Sirococcus*. Thus, a synthetic polypeptide having an amino acid sequence of SEQ ID NO: 1 (i.e. sequence of the cutinase polypeptide from *Sirococcus conigenus*) is within scope of this invention.

It must be understood that sequence of the gene or a polypeptide obtained from a strain may be modified so that the activity of the encoded polypeptide or fragment is not essentially altered and the same applies to possible post-translational modifications or modifications of synthetic polynucleotide or polypeptide. Typical modification of nucleotides encoding the polypeptide is codon optimization in order to enhance production in foreign production hosts. Examples of post-translational modifications are glycosylation, phosphorylation or digestion to smaller fragments.

In a preferred embodiment the polypeptide of the invention or a fragment thereof is produced using recombinant technology.

The invention is also directed to recombinant polynucleotides encoding the polypeptides of the invention. Recombinant polynucleotide is isolated from the genome of the donor organism, or amplified with the genome of the donor organism as the template, or synthesized on the basis of nucleotide data on the genome of the donor organism and transferred to a production organism. It is believed that optimal codons help to achieve faster translation rates and high accuracy in various host organisms, thus, a skilled man understands that also codon optimized sequences are within scope of this invention.

Polypeptides or fragments of this invention or polynucleotides encoding them can be identified, isolated, cloned and produced by methods known within the art.

Vectors carrying the nucleotide encoding the polypeptide or a fragment of this invention are also within the scope of this invention. Vectors can be produced by methods known within the art. Typically the expression vector contains means (at least a promoter and a termination signal operably linked to a polypeptide to be produced) for regulating the translation in desired production organism and optionally means for selection and site-directed transformation. A vector can also contain a signal sequence optimal to a production host.

The vector is then transformed to a host organism, usually a host cell. A stable transformant is preferred and it is also a requirement for large scale production. Any method known to the art may be used. Suitable hosts include fungi, yeasts, bacteria as well as animal and insect cells. Filamentous fungi such as *Trichoderma* and *Aspergillus* are examples of suitable fungal hosts, *Saccharomyces, Hansenula, Kluyveromyes* and *Pichia* are examples of suitable yeast hosts and *Bacillus, Escherichia, Streptomyces, Lactobacillus, Lactococcus* and *Pseudomonas*, are examples of suitable bacterial hosts.

Host is then cultivated under conditions allowing the expression of the desired polypeptide. The expression level may be increased by known methods such as using multiple copies of the gene to be translated or expressing the gene under a strong promoter such as *Trichoderma* cbh1 or using a host in which one or more endogeneous genes have been turned on or deleted. E.g. Gellissen (2005) describes recombinant production of polypeptides in various host systems.

In preferred embodiment the polypeptide (or the fragment) is secreted to the culture medium. The preparation may thus be the spent culture medium containing the polypeptide (usually after the separation of the cells). However, it is also possible to decompose the host cells (if the polypeptide product is not secreted) and thereby release the polypeptide for use or for recovery. The polypeptide can be purified to a higher degree of purity by known methods such us filtration, concentration, affinity methods etc. and formulated to the final product, if needed. In addition, depending on the application it is possible that the preparation also contains the production host.

In this connection "an enzyme preparation" is any composition comprising the polypeptide(s) or fragment(s) of the invention. Optionally other enzymes and components (such as stabilizers, surface active agents or buffering agents) may be present depending on the field of use. For example, the polypeptide of the invention can be used as a component of a plant material degrading enzyme cocktail containing any of the following enzymatic activities: e.g. protease, cellulase, ligninase, beta-glucosidase, hemicellulase, xylanase, alpha-amylase, amyloglucosidase, pectinases, laccase, peroxidase, lipase or expansin. Furthermore, e.g. protease, alpha-amylase, lipase, cellulase, xylanase, beta-glucanase, pectinase, lipoxygenase, peroxidase or laccase can be used in a detergent composition in combination with the polypeptide of the current invention. The polypeptide in the preparation may be in any form as discussed above.

In one embodiment of the invention the polypeptide is obtained by transforming a microorganism with a vector carrying the polynucleotide encoding the polypeptide. Stable transformation, e.g. integration of the production construct to the genome of host, is preferred. Host cell is then cultured in conditions that are suitable for expression of the polynucleotide. These conditions greatly depend on type of the host. Preferably the polypeptide is recovered by collecting the culture media where the polypeptide is secreted but also other means are possible.

Within the scope of this invention is also a method of hydrolysis of ester bonds where material containing ester bonds is contacted with the polypeptide (or a fragment) of this invention under conditions suitable for hydrolysis.

The method is suitable in releasing cutin or suberin monomers or oligomers from plant materials for the production of cutin or suberin derived chemicals such as polymer additives, polyesters, polyurethans, functionalized polymers, plastisizers, lubricants, compatibilizers, dispertants, base oils, corrosion inhibitors, grease thickeners, biodiesel, alkyd resins, polyurethane resins, drying oils, printing ink additives, wetting agents, viscosity modifiers, emulsifiers, stabilizers, coatings, texturizing additives, antioxidants, dyes, flavor compounds, nutrition supplements, cosmetic products, medicines (e.g. for UV-protection, anti-aging, treating hypercholestemia, preventing mutagenesis and adsorbtion of dietary carcinogens), texturized fats, health beneficial fats, or as reactants of trans- or interesterification reactions.

One particular embodiment is a method of treating agricultural or food raw materials or by-products obtained for example from vegetables, fruits, grapes, berries or cereals with the polypeptide or the fragment of the invention for facilitating the release of bioactive compounds (for examples polyphenolics) from the native biomatrix or for opening the plant surface structure for other degrading enzymes, for example, cellulases, ligninases, hemicellulases, pectinases or xylanases. In addition, the treatment with the polypeptide or the fragment of the invention may facilitate processing these materials.

Another embodiment is a method of treating wood raw materials, pulp and paper products, or process wastes or waters, or by-products with said protein for releasing suberin oligomers or monomers and/or for facilitating processing of the wood or wood-derived materials using the polypeptide or the fragment of this invention.

Another embodiment is a method of modifying materials used in textile production, electronic industry or in biomedicine with said protein in applications in which increasing the hydrophilicity of these materials is required using the polypeptide or the fragment of this invention.

One embodiment is a method of modifying synthetic or other man-made polyester fibres or textiles using the polypeptide of the fragment of this invention.

Still further embodiment is a method of removing stickies or fat from laundry and dishes using the polypeptide or the fragment of this invention.

Another embodiment is a method of releasing flavor-enhancing fatty acids from milk-fat to dairy products using the polypeptide or the fragment of this invention.

Another embodiment is a method of degrading toxic or harmful ester compounds such as pesticides or plastics using the polypeptide or the fragment of this invention.

Another embodiment is a method of enhancing the pharmacological effects of chemicals used in agriculture using the polypeptide or the fragment of this invention.

The various embodiments of this invention, especially the structural and functional properties of the polypeptide having SEQ ID NO: 1 or smaller fragments thereof (smaller polypeptides), can be combined without restriction.

The above-described embodiments and examples and the attached drawings are given for illustrative purposes and are intended to be non-limiting. The scope of the invention is defined in the following claims which are to be interpreted in their full breadth and taking equivalents into account.

EXAMPLES

Example 1. Assay Procedures

1. Cutinase Assay Using $^3$H-Labeled Cutin

Apple cutin was isolated as described previously by Halonen et al. (2009). The extent of cutin hydrolysis was determined using $^3$H-labeled cutin as the substrate by a modification of a previously described method (Davies et al., 2000). In this method the amount of radioactive hydrolysis products released into the solution from the cutin substrate are measured.

The labelled cutin (specific activity $4 \cdot 10^6$ dpm/mg) was mixed with unlabelled cutin to achieve a suitable specific activity for radioactivity measurements. 50 µl of enzyme sample was incubated in the presence of 1.2 mg $^3$H-cutin in a total volume of 200 µl. The reaction mixtures were buffered with McIlvaine. After incubation the reaction mixtures were centrifuged and 150 µl of the supernatants were analyzed using a scintillation counter. All samples were analyzed in duplicates and the average dpm values were calculated. Blank samples with buffer instead of the enzyme solution were used as controls and the values obtained were subtracted from the values obtained with the enzyme samples.

2. p-Nitrophenylbutyrate Esterase Assay

Esterase activity was determined using p-nitrophenyl butyrate (pNPB) as the model substrate by a modification of the method described previously by Davies et al. (2000). The reaction mixtures (300 µl) contained 2 mM pNPB, 0.5% (w/v) Triton X-100, McIlvaine buffer and 50 µl of the enzyme sample. The change in absorbance was monitored at 340 nm and at 25° C. p-Nitrophenol was used as the standard for the calculation of the initial velocities.

3. Triglyceride Hydrolysis Assay

Triglyceride hydrolyzing activities of the cutinases were determined using an emulsion of Bertolli olive oil (Unilever) as the substrate essentially as described by Kontkanen et al. (2004). An emulsification reagent was prepared by dissolving 2.5 g of gum arabic from acacia tree into 47% (v/v) glycerol. To 70 ml of the emulsification reagent, 30 ml of olive oil was added and the mixture was homogenized mechanically. The reaction mixtures contained 100 µl of the enzyme sample, 900 µl of McIlvaine buffer, pH 4.5, and 1 ml of the olive oil emulsion. The reaction mixtures were incubated at 40° C. under magnetic stirring for 10 min and the reactions were stopped by placing the tubes in a boiling water bath for 5 min. Then 2 ml of acetone:ethanol (1:1) was added and the phases were allowed to separate. The concentration of free fatty acids was determined from the upper liquid layer using the Free Fatty Acids, Half Micro Test (Roche). All samples were analyzed in duplicates.

4. Determination of Protein Concentrations

The commercial BioRad DC Protein Assay kit (500-0112) was used according to the instructions by the manufacturer with bovine serum albumin as the standard.

Example 2. Screening of Microbes for Polyester Hydrolyzing Activity 55 microbes (mostly fungal strains) from the VTT Culture Collection (Finland) were grown in the presence of suberin in Yeast Peptone or Yeast Nitrogen Base media under slightly acidic conditions and analyzed for suberinolytic activity. Degradation of suberin was analyzed by GC/MS from suberin samples withdrawn from the cultures. For analysis by GC/MS the solid samples were freeze dried. The dry samples were extracted consecutively with hexane and ethanol for lipophilic and hydrophilic compounds, respectively. The extractions were done by Dionex ASE 200 Accelerated Solvent Extraction System. The temperatures used were 90° C. for hexane extractions and 100° C. for ethanol extractions. The pressure was 100 bar in both cases and the extraction time was five minutes.

The GC-MS-instrument used for the analysis of the extracts for suberin monomers consisted of an Agilent 6890A GC and 5973N MS. The column used was a Nordion NB-54 with 5% phenylmethylpolysiloxane stationary phase. Heptadecanoic acid (100 μg) was added to the samples as an internal standard prior to silylating with N,O-bis(trimethylsilyl)trifluoroacetamide and trimethylchlorosilane. The temperature program was: 100° C.→15° C.→280° C. (18 min). The data collected was in the mass range from m/z 40-800 amu. Increased amount of long fatty acids, such as hydroxy fatty acids and diols, was used as the indicator for suberin degradation during the cultivations. The ability of the microbes to degrade suberin was also evaluated visually during the cultivations. Furthermore, the growth of the microbes in the absence and presence of suberin was monitored. *Sirococcus conigenus* was identified as a producer of suberinolytic polyesterases by the methods used.

Example 3. Cloning and Sequencing of the *Sirococcus conigenus* Cutinase (ScCut) Gene A fragment of the gene encoding the *Sirococcus conigenus* cutinase (ScCut) enzyme was amplified by PCR (polymerase chain reaction). Genomic DNA of *S. conigenus* was used as the template. The degenerate primers used were designed on the basis of sequences for fungal cutinases and cutinase-like genes obtained from the GenBank sequence database. These genes were from the fungi *Aspergillus oryzae* (BAA92327), *Pyrenopeziza brassicae* (CAB40372) and *Botrytis cinerea* (XP_001554721). Two different sets of primers were used: in the first set the codon usage of the fungi was not taken into account and in the second set the primers were modified to reflect the codon usage of *S. conigenus* (Table 1). Dynazyme EXT DNA polymerase (Finnzymes, Finland) was used in the reactions. In the touchdown PCR program used for amplification, the annealing temperature was lowered after every cycle (Table 2). (SEQ ID NO:s 4 to 11)

TABLE 1

Degenerate primers used for amplification

| Primer | Strand | Codon usage taken into account | Sequence (5'-3') |
|---|---|---|---|
| AsKod1aF | coding | yes | TTCGCYCGYGGYACYTCYGA GCCYGGYAA |
| AsKod1bF | coding | yes | GTCATGTCYGGYTAYTCYCAR GG |
| AsKod2aR | non-coding | yes | GGRTCRCCGAARATGAC |
| AsKod2bR | non-coding | yes | CCYTGRGARTARCCRGA |
| As1aF | coding | no | TTYGCIMGIGGIACIWSI GARCCIGGIAA |
| As1bF | coding | no | GTIATGWSIGGITAYWSI CARGG |
| As2aR | non-coding | no | GGRTCICCRAAIATIAC |
| As2bR | non-coding | no | CCYTGISWRTAICCISW |

In the table I indicates inosine (n in sequence listing), Y is C or T, R is A or G, W is A or T and S is G or C.

TABLE 2

Touchdown PCR-program for amplification of the fragment of the ScCut gene

| Step | Incubation time and temperature |
|---|---|
| 1 | 94° C. for 45 seconds |
| 2 | 50° C. for 1 minutes-1° C./cycle |
| 3 | 72° C. for 3 minutes |
| 4 | 14 times back to step 1 |
| 5 | 94° C. for 45 seconds |
| 6 | 36.9° C. for 1 minute |
| 7 | 72° C. for 3 minutes |
| 8 | 25 times back to step 5 |
| 9 | 72° C. for 10 minutes |

A fragment of 329 bp was amplified with the primers AsKod1aF and As2aR. The purified fragment was cloned into the pCR2.1 vector according to the instructions by the manufacturer (Invitrogen). The vector was transformed to *Escherichia coli* DH5α by electroporation according to the instructions of the TOPO TA-cloning kit manual (Invitrogen). Plasmid DNA was isolated from the transformants using the QIAprep Spin miniprep kit (Qiagen). The fragment cloned to the vector was sequenced using the reagents of the BigDye Terminator v3.1 Cycle Sequencing Kit (Applied Biosystems, USA) according to the instructions by Platt et al. (2007). M13 primers (5'-GTA AAA CGA CGG CCA GT-3' and 5'-CAG GAA ACA GCT ATG AC-3', SEQ ID NO: 12 and SEQ ID NO: 13, respectively) were used for sequencing. According to a blastX search of DNA-databases, the sequence of the fragment was similar to sequences present in several fungal cutinase genes.

Ligation mediated PCR (Fors et al., 1990) was used for obtaining the whole sequence for the ScCut gene. Genomic DNA was digested with the blunt-end-generating restriction enzymes BmgBI, EcoRV, FspI, NruI and RsaI. The fragments were purified (QiaQuick PCR-purification Kit, Qiagen) and ligated in a linker mixture containing linker I: 5"-G CG GTG ACC CGG GAG ATC TGA ATT C-3' and linker II: 5'-GAA TTC AGA TCT-3' primers (SEQ ID NO: 14 and SEQ ID NO: 15, respectively) with T4 ligase. Ligase and unligated linkers were removed after the reaction using the QiaQuick PCR-purification Kit (Qiagen).

Four primers were designed (Table 3) on the basis of the sequence of the fragment amplified using the degenerate primers. In the first PCR reactions, the fragments were amplified using the primers Cut2R and linker I (reaction a) and Cut1F and linker I (reaction b). In the second PCR reactions the PCR products from the first reactions were used as the templates. Fragments were amplified using the primer pairs Cut1R and linker I (product from reaction a as the template) and Cut2F and linker I (product from reaction b as the template). Dynazyme EXT DNA polymerase (Finnzymes, Finland) was used in these PCRs and the program used was: 94° C. for 3 minutes followed by 30 cycles of 94° C. for 1 minute, 60° C. for 2 minutes, 72° C. for 2 minutes. The final extension was carried out at 72° C. for 10 minutes. Products from the second PCR reactions were gel purified and sequenced directly with either primer Cut1R (products from the PCR reaction a) or primer Cut2F (products from the PCR reaction b) to obtain the sequence of the ScCut gene. No introns could be identified in the sequence.

TABLE 3

Primers used for ligation mediated PCR (SEQ ID NO's: 16 to 19).

| Primer | Sequence (5'-3') | PCR-reaction |
|---|---|---|
| Cut1F | AATGTTGGCCGGGTAGTCGAC | reaction I a |
| Cut1R | GGACCATGTCGCAGGTCAACTCG | reaction II a |
| Cut2F | TTGACAGCAGCGAAGAAGGGC | reaction II b |
| Cut2R | GCAGCTGGTGCACAACGCGGCCAA | reaction I b |

The gene encoding ScCut was amplified using the primers binding upstream of the ScCut gene start codon (SconCutF: 5'-CAG GTC GTA CTG GAT TTC TG-3', SEQ ID NO: 20) and downstream of the stop codon (SconCutR: 5'-ACA GAA GTT TCC TGC CCC TT-3', SEQ ID NO: 21). The PCR program used was: 94° C. for 5 minutes followed by 25 cycles of 94° C. for 45 seconds, 50° C. for 1 minute and 72° C. for 3 minutes. The final extension was carried out at 72° C. for 10 minutes. The Phusion DNA polymerase (Finnzymes, Finland) was used in the reaction. The fragment of the correct size was gel purified and 3'-A overhangs were added to the fragment in a Dynazyme DNA polymerase (Finnzymes, Finland) catalyzed reaction. The fragment was cloned to pCR2.1 vector and the resulting plasmid was transformed into *Escherichia coli* DH5α. The fragment was sequenced using M13 primers and the primers SconCutF and SconCutR.

The sequence was then compared to known cutinase sequences (FIG. 1) by ClustalW using default settings and Blosum62 as the substitution matrix (Thompson et al., 1994).

Example 4. Cloning and Expression of the ScCut Cutinase Gene

The *Sirococcus conigenus* cutinase (ScCut) gene (SEQ ID NO: 2) was codon optimized (SEQ ID NO: 3) for expression in *Pichia pastoris* and synthesized by GenScript (USA). Cloning and expression was carried out essentially as described in the Invitrogen User Manual for Expression of Recombinant Proteins in *Pichia pastoris* (revision date 7 Sep. 2010, Manual part no. 25-0043). The gene was supplemented with a sequence encoding a C-terminal His-tag to enable one-step purification of the ScCut enzyme by immobilized metal affinity chromatography (IMAC). The original secretion signal sequence of the gene was predicted using the SignalP online tool and omitted from the fragment. To facilitate cloning EcoRI and NotI restriction sites were inserted at the 5' and 3' ends of the fragment, respectively. The gene was isolated from the plasmids sent by GenScript by digestion with EcoRI and NotI and the gene fragment was ligated into the expression vector pPicZa-A (Invitrogen) in which it was fused in frame with the *Saccharomyces cerevisiae* α-factor secretion signal sequence. The vector contained the strong methanol inducible AOX1 promoter for expression of the gene. The constructs were transformed into *Escherichia coli* and ten transformant colonies were screened for the correct insert by PCR. Plasmid DNA was isolated from five of the positive clones and the DNAs were analyzed by restriction digestion analysis and by sequencing.

*P. pastoris* X-33 was cultivated aerobically in Yeast Extract Peptone Dextrose broth at 30° C. The cells were harvested at the optical density (600 nm) of between 1.3 and 1.5 by centrifugation. The cell pellet was washed with ice cold water and with ice cold 1 M sorbitol. After centrifugation the cells were suspended in 1/125 of the original culture volume in 1 M sorbitol and kept on ice. DNA (7.5 µg) linearized with PmeI digestion was mixed with 80 µl of cell suspension and the cells were transformed by electroporation. 1 ml of 1 M sorbitol was added and the cells were incubated for 1 h at room temperature and plated on Yeast Extract Peptone Dextrose agar plates containing 100 µg/ml of zeocin.

The transformants were grown overnight in Buffered Glycerol Complex Medium at 30° C. When the optical densities (600 nm) reached 2.5, the cells were collected by centrifugation and suspended into Buffered Methanol Complex Medium containing 0.5% (v/v) methanol to optical density of 0.45 at 600 nm. The cells were grown aerobically at 30° C. for 6 days. Methanol was added each day to 0.5% (v/v) of total volume to compensate for evaporation. Expression of the cutinase genes were followed by measuring the pNPB-esterase activity at pH 3.5 (as described in Example 1) of the growth supernatants. The most efficient esterase producing transformant was chosen for ScCut production.

Example 5. Production and Purification of the ScCut Enzyme 1 liter of Buffered Methanol Complex Medium was inoculated with a 50 ml culture of the *P. pastoris* transformant chosen for cutinase production (described in Example 4) and the cells were grown aerobically at 30° C. for 3 days. pNPB-esterase activity at pH 3.5 (as described in Example 1) was monitored (FIG. 2) and methanol was added daily to 0.5% (v/v) to the culture. After the cultivation the cells were removed by centrifugation and the pH of the supernatant was adjusted to pH 8.0 with NaOH. The supernatant was filtered and 3 g of trisodium citrate-2-hydrate was added to prevent the formation of the phosphate precipitates. 1 mM of the protease inhibitor phenylmethanesulfonyl fluoride was added to the supernatant.

The C-terminal His-tag with 6 histidines fused to the ScCut enabled the one step purification of the enzyme by IMAC. Ni-NTA-Agarose (Qiagen, 30210) packed in a XK16 column (Pharmasia) with a column volume of 4 ml was used in the purification. The column was equilibrated with starting buffer containing 50 mM Na-phosphate, pH 8.0, and 300 mM of NaCl. The sample (850 ml) was applied at a flow rate of 1 ml/min. The column was eluted with starting buffer supplemented with 10 mM of imidazole and fractions having pNPB-esterase activity at pH 3.5 (determined as described in Example 1) were collected. The buffer of these fractions was changed to 1:10 McIlvaine, pH 7, by ultrafiltration and dilution. SDS-PAGE analysis of the ScCut containing fractions showed a protein band with a molecular mass of around 20 kDa. This corresponds well with the molecular mass of 18.2 kDa calculated on the basis of the amino-acid sequence. The ScCut was purified to a virtual homogeneity by IMAC. The purified protein had a specific pNPB-esterase activity of 360 nkat/mg at pH 3.5. The purified sample was used for further enzyme characterization experiments.

Example 6. pH-Profile and -Stability of ScCut

The pH-profile of ScCut was studied between pH 2 and 8 for cutinolytic activity (using $^3$H-cutin as the substrate) and for pNPB-esterase activity. The assay procedures described in Example 1 were used in the experiments. The reaction mixtures were buffered with McIlvaine buffer. The pH profile for cutin hydrolysis by ScCut was determined by incubating the enzyme samples at 40° C. for 24 h at a protein dilution of 0.2 mg/ml. The pNPB-esterase activities were determined at 25° C. using a protein dilution of 7.4 μg/ml. The results are presented in FIG. 3. With $^3$H-cutin as the substrate the values are presented as percentages of the maximum. ScCut showed a pH-optimum for cutin hydrolysis between 3.5 and 4.5, whereas the pH optimum for pNPB-esterase activity was between 4.5 and 5. With both $^3$H-cutin and pNPB as the substrates, hydrolysis was detected across a broad pH range. Activity was detectable below pH 3 with both substrates. The cutin hydrolyzing capacity of ScCut was compared to the results reported for the most acidic cutinases known [*Botrytis cinerea* cutinase (Shishiyama et al., 1970; Salinas et al., 1986; van der Vlugt-Bergmans et al., 1997), *Venturia inaequalis* cutinase (Köller and Parker, 1989) and *Alternaria brassicola* cutinase (Trail and Köller, 1993)]. It can be concluded on the basis of the comparison that cutin hydrolysis at pHs of below 5.0 has not been shown for any other cutinase than ScCut.

pH stability was determined at the same pH range as above by incubating the enzyme samples at 40° C. for 24 h in McIlvaine buffer. After incubation the samples were diluted by 1:5 with McIlvaine buffer at pH 7 and the pNPB-esterase activities were determined. The reaction mixtures were buffered with 0.5 M Na-phosphate buffer pH 7 in order to bring all samples to equal pH. The residual pNPB-esterase activities were determined and compared to the initial activity determined at pH 7.0. The results are presented in FIG. 4. ScCut was stable over a wide range of pH-values. It showed over 90% stability within the pH range of 3.5-7.5. The stability was somewhat lower outside this range, but clear residual activity was detected. The results show that the enzyme is both stable and active under various pHs and could be suitable for many different applications because of this type of robustness.

Example 8. Temperature Stability of ScCut

The temperature stability of ScCut was studied by determining the half lives at different temperatures. ScCut was incubated at the concentration of 37 μg/ml in McIlvaine buffer at pH 4.5. pNPB-esterase activities were measured from each sample at multiple time points during two days. The results were plotted on a semi-log scale (log of the relative activity versus time), and the half-lives were calculated from the slope of the trend line. No decrease in the activity was detected at 4° C. and at 25° C. during the two-day incubation. The half-lives determined at the other temperatures used are presented in Table 4. The results show that ScCut is stable for use in detergent and plant material processing applications.

TABLE 4

| Half-lives of ScCut at different temperatures | |
|---|---|
| Temperature | Half-life |
| 42° C. | 76 h |
| 55° C. | 9 h |
| 65° C. | 4 h |
| 85° C. | 24 min |

Example 9. Hydrolysis of p-Nitrophenyl Esters of Different Chain Lengths

Figure 5:
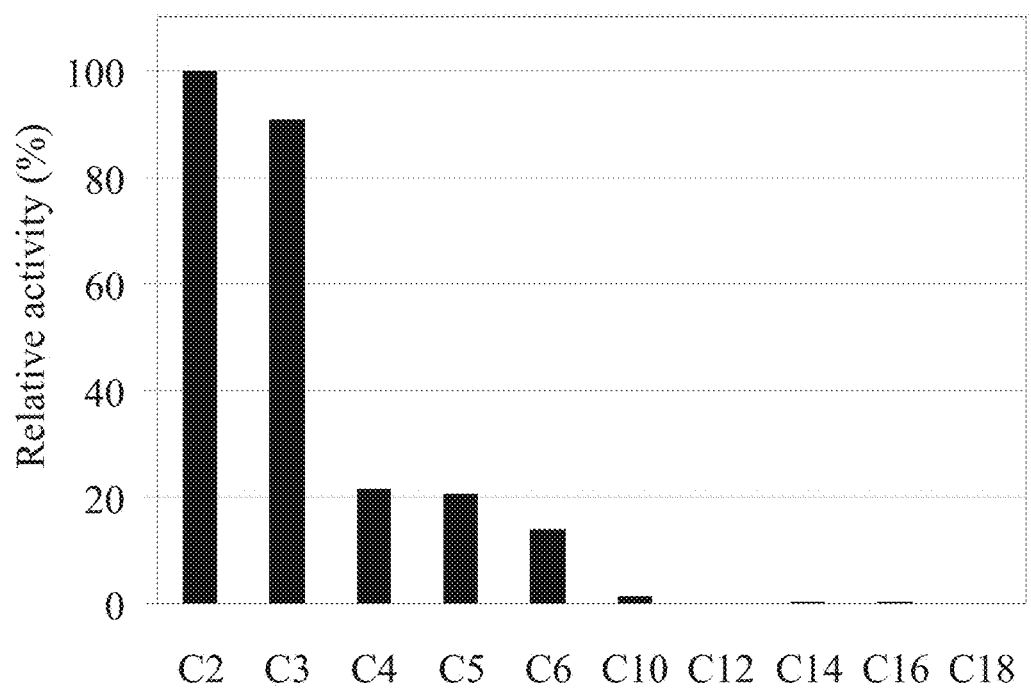
FIG. 5. Effect of fatty acid chain length on the esterolytic activity of ScCut cutinase determined at 25° C. and at pH 4.5.

The activity of ScCut towards fatty acid esters with different carbon chain lengths was determined at pH 4.5 using the procedure for the esterase assay for pNP-butyrate hydrolysis (described in Example 1). The fatty acid moieties of the p-nitrophenyl esters used as the substrates were: acetate (C2), propionate (C3), butyrate (C4), valerate (C5), caproate (C6), caprate (C10), laurate (C12), myristate (C14), palmitate (C16) and stearate (C18). The substrate concentration of 2 mM was used in the reaction mixtures. The results shown in FIG. 5 indicate a preference towards pNP-esters of short chain fatty acids by ScCut. This specificity profile is typical for cutinases.

Example 10. Hydrolysis of Cutin, Suberin and Triglycerides by ScCut

The natural, extractive free substrates, apple cutin and birch bark suberin were isolated as described previously by Halonen et al. (2009) for estimation on ScCut catalyzed hydrolysis of these materials. The reaction mixtures comprised 50 mg/ml of cutin or suberin and 100 nkat/ml of ScCut (as pNPB-esterase activity determined at pH 4.5) and McIlvaine buffer at pH 4.5. The reaction mixtures were incubated for 48 h at 40° C. and extracted with methyl tertiary butyl ether (MTBE) in order to recover the cutin and suberin oligo- and monomers released from the solid substrate by enzyme action. Free fatty acids in the MTBE extract were analysed directly and after alkali hydrolysis of released oligomers using the Free Fatty Acids Half Micro Test (Roche) as described previously by Kontkanen et al. (2009). The amounts of fatty acids released by ScCut treatment were compared to the amount of fatty acids released in total alkali hydrolysis of the substrates. Treatment with ScCut released 1.4 mol-% and 3.0 mol-% of the total fatty acids from suberin and cutin, respectively.

The specific lipase (triglyceride hydrolyzing) activity was determined at pH 4.5 with olive oil as the substrate as described in Example 1. ScCut showed a specific lipase activity of 70.3±3.7 nkat/mg.

REFERENCES

Agrawal P. B. (2005) The performance of cutinase and pectinase in cotton scouring. PhD Thesis, University of Twente, the Netherlands.

De Barros D. P. C., Fonseca L. P., Fernandes P., Cabral J. M. S., Mojovic, L. (2009) Biosynthesis of ethyl caproate and other short ethyl esters catalyzed by cutinase in organic solvent. J Mol Cat B Enzym 60:178-185.

Carvalho C. M. L, Aires-Barros M. R., Cabral J. M. S. (1998) Cutinase structure, function and biocatalytic applications. El J Biotech 1:160-73.

Davies K. A., De Lorono I., Foster S. J., Li D., Johnstone K., Ashby A. M. (2000) Evidence for a role of cutinase in pathogenicity of Pyrenopeziza brassicae on brassicas. Physiol Mol Plant Pathol 57:63-75.

Fors L., Saavedra R. A., Hood L. (1990) Cloning of the shark Po promoter using a genomic walking technique based on the polymerase chain reaction. Nucleic Acids Research 18:2793-2799.

Gellissen G. (ed.) (2005) Production of recombinant proteins. Novel microbial and eukaryotic expression systems. Wiley-VCH Verlag Gmbh & Co. Weinheim, Germany.

Halonen P., Reinikainen T., Nyyssold A., Buchert J (2009) A high throughput profiling method for cutinolytic esterases. Enz Microbial Technol 44:394-399.

Kontkanen H., Tenkanen M., Fagerstrom R., Reinikainen T. (2004) Characterisation of steryl esterase activities in commercial lipase preparations. J Biotechnol 108:51-59.

Kontkanen H., Westerholm-Parvinen A., Saloheimo M., Bailey M., Rättö M., Mattila I. Mohsina M., Nakari-Setälä, T., Buchert J. (2009) A novel polyesterase from Coprinus cinereus hydrolyzing cutin and suberin. Appl Environ Microbiol 75:2148-2157.

Köller W., Parker D. M. (1989) Purification and characterization of cutinase from Venturia inaequalis. Phytopathology 79:278-283.

Pinto-Sousa A. M. C., Cabral, J. M. S., Aires-Barros M. R. (1994) Ester synthesis by a recombinant cutinase in reversed micelles of a natural phospholipid. Biocat 9:169-179.

Pio T. F., Macedo, G. A. (2009) Cutinases: properties and industrial applications, Adv Appl Microbiol 66:77-95.

Platt, A. R., Woodhall, R. W., George Jr., A. L. (2007) Improved DNA sequencing quality and efficiency using an optimized fast cycle sequencing protocol. BioTechniques 43:58-60.

Salinas J., Warnaar F., Verhoeff K. (1986) Production of cutin hydrolyzing enzymes by Botrytis cinerea in vitro. J. Phytopathology. 116:299-307.

Shishiyama J., Araki F., Akai S. (1970) Studies on cutin-esterase II. Characteristics of cutin-esterase from Botrytis cinerea and its activity on tomato-cutin. Plant Cell Physiol 11: 937-945.

Thompson J. D., Higgins D. G., Gibson T. J. (1994) CLUSTAL W: improving the sensitivity of progressive multiple sequence alignment through sequence weighting, position-specific gap penalties and weight matrix choice. Nucleic Acids Res 22:4673-4680.

Trail F., Köller W. (1993) Diversity of cutinases from plant pathogenic fungi: purification and characterization of two cutinases from Alternaria brassicicola. Physiol Mol Plant Pathol 42:205-220.

van der Vlugt-Bergmans C. J. B., Wagemakers C. A. M., van Kan, J. A. L. (1997) Cloning and expression of the cutinase A gene of Botrytis cinerea. Molecular Plant-Microbe Interactions 10:21-29.

The invention claimed is:

1. A polypeptide comprising the amino acid sequence of SEQ ID NO: 1 or an active fragment of said polypeptide, further comprising at least one esterase activity, wherein the activity is a cutinase activity, a suberinase activity or a lipase activity, or any combination of said activities, and wherein the polypeptide or the fragment is active towards polyesters at pH range from 2.5 to 7.5.

2. The polypeptide or fragment of claim 1, wherein the activity is a combination of a cutinase, a suberinase and a lipase activity.

3. The polypeptide or fragment of claim 1, wherein the polypeptide or fragment is active towards polyesters at pH below 5.

4. The polypeptide or fragment of claim 1, comprising at least 77 amino acids.

5. The polypeptide or fragment of claim 1, wherein the polypeptide or fragment is derived from *Sirococcus*.

6. An enzyme preparation comprising a polypeptide having an amino acid sequence of SEQ ID NO: 1 or an active fragment of said polypeptide, further comprising at least one esterase activity, wherein the activity is a cutinase activity, a suberinase activity or a lipase activity, or any combination of said activities, and wherein the polypeptide or the fragment is active towards polyesters at pH range from 2.5 to 7.5.

7. A method of hydrolysis comprising the step of contacting a material containing ester bonding with the polypeptide of claim 1 under conditions suitable for hydrolysis.

8. Method of claim 7, further comprising treating agricultural or food raw materials or by-products obtained from vegetables, fruits, grapes, berries or cereals.

9. Method of claim 7, further comprising treating wood raw materials, pulp and paper products, or process wastes or waters, or by-products with said protein.

10. Method of claim 7, further comprising modifying synthetic or other man-made polyester fibres or textiles with said protein.

11. Method of claim 7, further comprising removing stickies or fat from laundry and dishes with said protein.

12. Method of trans- or interesterification comprising the step of contacting a material to be esterified with the polypeptide of claim 1 under conditions suitable for esterification.

13. The polypeptide or fragment of claim 1, wherein the polypeptide or fragment is encoded by nucleotides 7-561 of SEQ ID NO: 3.

14. The polypeptide or fragment of claim 1, wherein the polypeptide or fragment includes a C-terminal His-tag enabling one-step purification of the polypeptide or fragment by immobilized metal affinity chromatography.

* * * * *

SEQUENCE LISTING

```
<160> NUMBER OF SEQ ID NOS: 21

<210> SEQ ID NO 1
<211> LENGTH: 202
<212> TYPE: PRT
<213> ORGANISM: Sirococcus conigenus
<220> FEATURE:
<221> NAME/KEY: SIGNAL
<222> LOCATION: (1)..(17)
<220> FEATURE:
<221> NAME/KEY: mat_peptide
<222> LOCATION: (18)..(202)

<400> SEQUENCE: 1

Met Lys Ser Thr Ile Leu Phe Ser Ala Leu Leu Ser Ser Gly Ala Leu
        -15                 -10                  -5

Ala Ala Pro Thr Val Val Glu Ala Val Glu Ala Arg Ala Ala Cys Ser
 -1   1               5                  10                  15

Asp Met Thr Ile Ile Phe Ala Arg Gly Thr Thr Glu Pro Gly Thr Val
                    20                  25                  30

Gly Thr Leu Ala Gly Pro Pro Phe Phe Ala Ala Val Lys Ser Gln Leu
                35                  40                  45

Gly Gly Arg Ala Thr Leu Thr Thr Gln Gly Val Asp Tyr Pro Ala Asn
            50                  55                  60

Ile Ala Gly Phe Leu Ala Gly Gly Asp Pro Ala Gly Ser Gln Thr Met
 65                  70                  75

Ala Asn Asp Val Lys Ala Ala Leu Ala Ala Cys Pro Asp Thr Lys Leu
 80                  85                  90                  95

Val Met Ala Gly Tyr Ser Gln Gly Gly Gln Leu Val His Asn Ala Ala
                   100                 105                 110
```

```
Lys Leu Leu Gly Gly Thr Met Ser Gln Val Asn Ser Ala Val Ile Phe
            115                 120                 125
Gly Asp Pro Asp Asn Gly Gln Pro Val Ala Gly Leu Ser Ala Ala Gln
        130                 135                 140
Thr Lys Ile Ile Cys His Ala Gly Asp Asn Ile Cys Gln Gly Gly Ala
    145                 150                 155
Leu Ile Leu Ala Pro His Leu Thr Tyr Gly Gln Asp Ala Gly Thr Ala
160                 165                 170                 175
Ala Ser Phe Val Ile Ala Ala Ala Gly Leu
                180                 185

<210> SEQ ID NO 2
<211> LENGTH: 609
<212> TYPE: DNA
<213> ORGANISM: Sirococcus conigenus

<400> SEQUENCE: 2
atgaagtcta ccattctctt ttcggccctc ctctcatcgg gtgctctggc agcacctacc      60
gttgtcgagg ccgttgaagc acgcgccgcc tgctcggaca tgaccattat ctttgcccgc     120
ggcaccaccg agccgggcac cgtcggcacc ctggctggtc cgcccttctt cgctgctgtc     180
aagtcccagt ggggcgggag ggccacgctg accacccagg gcgtcgacta cccggccaac     240
attgccggct tcctggccgg cggcgacccg gcgggagcc agaccatggc caacgacgtc      300
aaggcggcgc tggcggcgtg ccccgacacc aagctggtca tggcgggcta ctcgcagggc     360
gggcagctgg tgcacaacgc ggccaagctc ttgggggggga ccatgtcgca ggtcaactcg     420
gccgtcatct ttggcgaccc ggacaacggc cagcccgtgg cgggcctgtc ggcggcccag     480
acgaaaatca tctgccacgc cggcgacaac atttgccagg gaggcgccct gatcctggcg     540
ccgcacctga cgtacgggca ggacgcgggc actgcagcct tttttgtgat cgcagcggcc     600
gggctttaa                                                             609

<210> SEQ ID NO 3
<211> LENGTH: 590
<212> TYPE: DNA
<213> ORGANISM: Sirococcus conigenus

<400> SEQUENCE: 3
gaattcgctc caaccgttgt cgaagcagtt gaggctagag ctgcctgttc tgacatgact      60
attatctttg ccagaggtac tacagaacct ggtacagttg aaccttggc aggaccacca     120 ttttcgcag ctgtcaagtc tcaattgggt ggtagagcta ctcttaccac tcagggagtt     180
gattacccag ccaacattgc aggtttcttg gcaggtggag atcctgctgg atcacaaaca     240
atggctaatg acgtcaaggc cgcattggct gcctgcccag ataccaaact tgttatggct     300
ggttatagtc aaggtggaca gttggtccat aacgctgcta agttgcttgg tggaactatg     360
tctcaagtta actccgccgt cattttttgga gatccagaca atggacaacc tgttgctggt     420
ttgtctgccg cacagacaaa aattatctgt catgctggtg acaatatttg ccaaggtgga     480
gctttgatcc ttgcccctca cttgacttac ggtcaggatg ctggaacagc tgcctctttc     540
gttatcgcag ctgccggtct tcatcaccat caccatcact aagcggccgc                590

<210> SEQ ID NO 4
<211> LENGTH: 29
<212> TYPE: DNA
<213> ORGANISM: Artificial Sequence
```

```
<220> FEATURE:
<223> OTHER INFORMATION: Primer

<400> SEQUENCE: 4
ttcgcycgyg gyacytcyga gccyggyaa                                             29

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gtcatgtcyg gytaytcyca rgg                                                   23

<210> SEQ ID NO 6
<211> LENGTH: 17
<212> TYPE: DNA
<213> ORGANISM: Artificial Sequence
<220> FEATURE:
<223> OTHER INFORMATION: primer

<400> SEQUENCE: 6
ggrtcrccga aratgac                                                          17

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
ccytgrgart arccrga                                                          17

<210> SEQ ID NO 8
<211> LENGTH: 29
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (6)..(6)
<223> OTHER INFORMATION: Inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: Inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (12)..(12)
<223> OTHER INFORMATION: Inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (15)..(15)
<223> OTHER INFORMATION: Inosine
<220> FEATURE:
```

```
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (18)..(18)
<223> OTHER INFORMATION: Inosine
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: modified_base
<222> LOCATION: (24)..(24)
<223> OTHER INFORMATION: Inosine
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: modified_base
<222> LOCATION: (27)..(27)
<223> OTHER INFORMATION: Inosine
<220> FEATURE:
<221> NAME/KEY: misc_feature
<222> LOCATION: (27)..(27)
<223> OTHER INFORMATION: n is a, c, g, or t

<400> SEQUENCE: 8
ttygcnmgng gnacnwsnga rccnggnaa                                             29

<210> SEQ ID NO 9
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (3)..(3)
<223> OTHER INFORMATION: Inosine
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (9)..(9)
<223> OTHER INFORMATION: Inosine
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (12)..(12)
<223> OTHER INFORMATION: Inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (18)..(18)
<223> OTHER INFORMATION: Inosine
<220> FEATURE:
<221> NAME/KEY: misc_feature
<222> LOCATION: (18)..(18)
<223> OTHER INFORMATION: n is a, c, g, or t

<400> SEQUENCE: 9
gtnatgwsng gntaywsnca rgg                                                   23

<210> SEQ ID NO 10
<211> LENGTH: 17
```

```
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (6)..(6)
<223> OTHER INFORMATION: Inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (12)..(12)
<223> OTHER INFORMATION: Inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (15)..(15)
<223> OTHER INFORMATION: Inosine
<220> FEATURE:
<221> NAME/KEY: misc_feature
<222> LOCATION: (15)..(15)
<223> OTHER INFORMATION: n is a, c, g, or t

<400> SEQUENCE: 10
ggrtcnccra anatnac                                                17

<210> SEQ ID NO 11
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (6)..(6)
<223> OTHER INFORMATION: Inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (12)..(12)
<223> OTHER INFORMATION: Inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (15)..(15)
<223> OTHER INFORMATION: Inosine
<220> FEATURE:
<221> NAME/KEY: misc_feature
<222> LOCATION: (15)..(15)
<223> OTHER INFORMATION: n is a, c, g, or t

<400> SEQUENCE: 11
ccytgnswrt anccnsw                                                17

<210> SEQ ID NO 12
<211> LENGTH: 17
<212> TYPE: DNA
<213> ORGANISM: Artificial Sequence
<220> FEATURE:
<223> OTHER INFORMATION: primer

<400> SEQUENCE: 12
```
gtaaaacgac ggccagt                                                          17

<210> SEQ ID NO 13
<211> LENGTH: 17
<212> TYPE: DNA
<213> ORGANISM: Artificial Sequence
<220> FEATURE:
<223> OTHER INFORMATION: primer

<400> SEQUENCE: 13
caggaaacag ctatgac                                                          17

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
gcggtgaccc gggagatctg aattc                                                 25

<210> SEQ ID NO 15
<211> LENGTH: 12
<212> TYPE: DNA
<213> ORGANISM: Artificial Sequence
<220> FEATURE:
<223> OTHER INFORMATION: primer

<400> SEQUENCE: 15
gaattcagat ct                                                               12

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
aatgttggcc gggtagtcga c                                                     21

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
ggaccatgtc gcaggtcaac tcg                                                   23

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
ttgacagcag cgaagaaggg c                                                     21

<210> SEQ ID NO 19
<211> LENGTH: 24
<212> TYPE: DNA
<213> ORGANISM: Artificial Sequence

```
<220> FEATURE:
<223> OTHER INFORMATION: primer

<400> SEQUENCE: 19
gcagctggtg cacaacgcgg ccaa                                              24

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
caggtcgtac tggatttctg                                                   20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
acagaagttt cctgcccctt                                                   20
```